(12) United States Patent
Deora et al.

(10) Patent No.: US 12,727,741 B2
(45) Date of Patent: Sep. 8, 2026

(54) SIPHON PROTECTION AND INFECTION PREVENTION OF AIR-WATER TUBE END CONNECTOR

(71) Applicant: Boston Scientific Scimed, Inc., Maple Grove, MN (US)

(72) Inventors: Aakash Deora, Marlborough, MA (US); Ryan Vincent William Pollock, Sterling, MA (US); Scott Edward Corbeil, Litchfield, NH (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 245 days.

(21) Appl. No.: 18/545,472

(22) Filed: Dec. 19, 2023

(65) Prior Publication Data

US 2024/0197160 A1 Jun. 20, 2024

Related U.S. Application Data

(60) Provisional application No. 63/433,958, filed on Dec. 20, 2022.

(51) Int. Cl.
*A61B 1/00* (2006.01)
*A61B 90/70* (2016.01)

(52) U.S. Cl.
CPC ...... *A61B 1/00144* (2013.01); *A61B 1/00142* (2013.01); *A61B 90/70* (2016.02); *A61B 2090/701* (2016.02)

(58) Field of Classification Search
CPC . A61B 1/00142; A61B 1/00144; A61B 1/121; A61B 1/125; A61B 90/70; A61B 1/00137
See application file for complete search history.

(56) References Cited

U.S. PATENT DOCUMENTS

| | | | | |
|---|---|---|---|---|
| 5,431,150 | A | 7/1995 | Yabe et al. | |
| 5,702,347 | A | 12/1997 | Yabe et al. | |
| 8,241,208 | B2 | 8/2012 | Jiang et al. | |
| 10,433,711 | B2 | 10/2019 | Ogura et al. | |
| 2005/0016886 | A1 | 1/2005 | Riley | |
| 2005/0065405 | A1 | 3/2005 | Hasegawa | |
| 2006/0258909 | A1* | 11/2006 | Saadat | A61B 46/10 600/121 |
| 2007/0293875 | A1 | 12/2007 | Soetikno et al. | |

(Continued)

OTHER PUBLICATIONS

Invitation to Pay Additional Fees dated Apr. 22, 2024 for International Application No. PCT/US2023/084845.

(Continued)

*Primary Examiner* — Aaron B Fairchild
(74) *Attorney, Agent, or Firm* — Seager, Tufte & Wickhem, LLP

(57) ABSTRACT

Systems and methods for preventing leaks from an endoscope end of a tube set during equipment changes between endoscopic procedures. An illustrative system may comprise a storage case and a cap. The storage case may comprise a base including a plurality of wells, an insert disposed in each well of the plurality of wells, and a lid configured to cover the base. The cap may have a housing extending from a first open end to a second closed end and defining a cavity between the first open end and the second closed end and may be configured to be removably disposed within a well of the plurality of wells.

12 Claims, 10 Drawing Sheets

(56) References Cited

U.S. PATENT DOCUMENTS

| | | | |
|---|---|---|---|
| 2009/0287052 | A1 | 11/2009 | Amos et al. |
| 2015/0119645 | A1 | 4/2015 | Baldwin |
| 2022/0192478 | A1 | 6/2022 | Pollock et al. |

OTHER PUBLICATIONS

International Search Report and Written Opinion for International Application No. PCT/US2023/084845, dated Jun. 11, 2024. (16 pages).

* cited by examiner

SIPHON PROTECTION AND INFECTION PREVENTION OF AIR-WATER TUBE END CONNECTOR

CROSS-REFERENCE TO RELATED APPLICATIONS

This application claims the benefit of U.S. Provisional Patent Application Ser. No. 63/433,958 filed on Dec. 20, 2022, the disclosure of which is incorporated herein by reference.

FIELD

This disclosure relates generally to medical fluid containers and methods, and particularly to a container and tube sets to supply fluid and/or gas to an endoscope.

BACKGROUND

Conventionally, endoscope devices have been widely used for performing diagnostic and/or therapeutic treatments. During endoscopic procedures, physicians may use a combination of air, irrigation, and lens wash as a means of flushing debris, cleaning optics, and insufflating the working lumen. For example, sterile water may be used to irrigate the working lumen during the procedure. Further, during endoscopic procedures, the video lens at the distal end of the endoscope, which is used to navigate and visualize target tissues, may be prone to becoming fouled with blood, mucous, and other debris during the procedure. The tube set used for providing irrigation fluid and/or lens wash fluid may be commonly used for a period of 24 hours across multiple endoscopic procedures. However, the same endoscope is not used for multiple patients and must be switched out between procedures. During the time the tube set connector connecting the fluid tubes to the endoscope is disconnected from the endoscope, the tube set needs to be placed somewhere. In some cases, the tube set is placed in a position that tends to leak water. For example, if the tube is left on the floor, the difference in the water level in the tube and water bottle may become conducive for siphon initiation. This may cause large water puddles which are a safety hazard for the occupants of the room as well the electronic equipment in the vicinity. Further, if the tube end connector is left open to the surroundings, the tube end becomes susceptible to transmitting infection.

It may be desirable to prevent siphoning of water from the water bottle after the cleaning as well as ensure the air-water end connector remains hygienic between procedures. It is with these considerations in mind that the improvements of the present disclosure may be useful.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary. Accordingly, while the disclosure is presented in terms of aspects or embodiments, it should be appreciated that individual aspects can be claimed separately or in combination with aspects and features of that embodiment or any other embodiment.

In a first example, a system for preventing leaks from an endoscope end of a tube set for use with an endoscope may comprise a storage case comprising a base including a plurality of wells, an insert disposed in each well of the plurality of wells, and a lid configured to cover the base. The system may further comprise a cap having a housing extending from a first open end to a second closed end and defining a cavity between the first open end and the second closed end, the cap configured to be removably disposed within a well of the plurality of wells.

Alternatively or additionally to any of the examples above, in another example, the insert may be sized and shaped to conform to an inner surface of the cap.

Alternatively or additionally to any of the examples above, in another example, the insert may comprise a perforated foam.

Alternatively or additionally to any of the examples above, in another example, the insert may comprise an embedded antibacterial or bacteriostatic material.

Alternatively or additionally to any of the examples above, in another example, the system may further comprise an antiseptic disposed within at least one well of the plurality of wells.

Alternatively or additionally to any of the examples above, in another example, the cap may be configured to be disposed over an outer surface of an endoscope end of a tube set.

Alternatively or additionally to any of the examples above, in another example, the system may further comprise a sealing member disposed within the cavity of the cap.

Alternatively or additionally to any of the examples above, in another example, the cap may further comprise a coupling mechanism, the coupling mechanism configured to releasably couple the cap to an endoscope end of a tube set.

In another example, a system for preventing leaks from an endoscope end of a tube set for use with an endoscope may comprise a clamp having a securing region and an actuation region, the actuation region configured to be actuated to selectively expand the securing region, a cap secured to a portion of the clamp, the cap having a housing extending from a first end to a second end and configured to be releasably secured to an endoscope end of a tube set, and a coupling mechanism positioned on a portion of the cap.

Alternatively or additionally to any of the examples above, in another example, the coupling mechanism may be configured to engage a mating feature on the endoscope end of the tube set.

Alternatively or additionally to any of the examples above, in another example, the securing region may comprise a first arm and a second arm.

Alternatively or additionally to any of the examples above, in another example, in an absence of an applied force, the first and second arm of the securing region may be biased towards a central axis of the clamp.

Alternatively or additionally to any of the examples above, in another example, the actuation region may comprise a first arm and a second arm.

Alternatively or additionally to any of the examples above, in another example, the first arm and the second arm of the actuation region may be configured to be biased towards a central axis of the clamp under an applied force to move the first arm and the second arm of the securing region away from the central axis of the clamp.

Alternatively or additionally to any of the examples above, in another example, the clamp may be configured to be releasably secured to a post of an endoscope tower.

In another example, a system for preventing leaks from an endoscope end of a tube set for use with an endoscope may comprise a clamp having a securing region and an actuation region, the actuation region configured to be actuated to selectively expand the securing region, a first cap secured to a portion of the clamp, the first cap having a housing extending from a first end to a second end and configured to be releasably secured to an endoscope end of a first tube set, the first tube set having a first coupling type, and a coupling mechanism positioned on a portion of the first cap.

Alternatively or additionally to any of the examples above, in another example, the coupling mechanism may be configured to engage a mating feature on the endoscope end of the first tube set.

Alternatively or additionally to any of the examples above, in another example, the securing region may comprise a first arm and a second arm.

Alternatively or additionally to any of the examples above, in another example, in an absence of an applied force, the first and second arm of the securing region may be biased towards a central axis of the clamp.

Alternatively or additionally to any of the examples above, in another example, the actuation region may comprise a first arm and a second arm.

Alternatively or additionally to any of the examples above, in another example, the first arm and the second arm of the actuation region may be configured to be biased towards a central axis of the clamp under an applied force to move the first arm and the second arm of the securing region away from the central axis of the clamp.

Alternatively or additionally to any of the examples above, in another example, the clamp may be configured to be releasably secured to a post of an endoscope tower.

Alternatively or additionally to any of the examples above, in another example, the first cap may be fixedly secured to the clamp.

Alternatively or additionally to any of the examples above, in another example, the first cap may be releasably secured to the clamp.

Alternatively or additionally to any of the examples above, in another example, the system may further comprise a second cap secured to a portion of the clamp, the second cap configured to be releasably secured to an endoscope end of a second tube set, the second tube set having a second coupling type different from the first coupling type.

In another example, a system for preventing leaks from an endoscope end of a tube set for use with an endoscope may comprise a clamp having a securing region including a first arm and a second arm and an actuation region including a first arm and a second arm, wherein the clamp has a generally "X" shape with a cut-out region at an intersection of the securing region and the actuation region, a cap secured to a portion of the clamp, the cap having a housing extending from a first end to a second end and configured to be releasably secured to an endoscope end of a tube set, and a coupling mechanism positioned on a portion of the cap.

Alternatively or additionally to any of the examples above, in another example, the cap may further comprise a sealing member.

These and other features and advantages of the present disclosure will be readily apparent from the following detailed description, the scope of the claimed invention being set out in the appended claims.

BRIEF DESCRIPTION OF THE DRAWINGS

The accompanying drawings, which are incorporated in and constitute a part of this specification, illustrate various exemplary embodiments and together with the description serve to explain the principles of the present disclosure.

Figure 1:
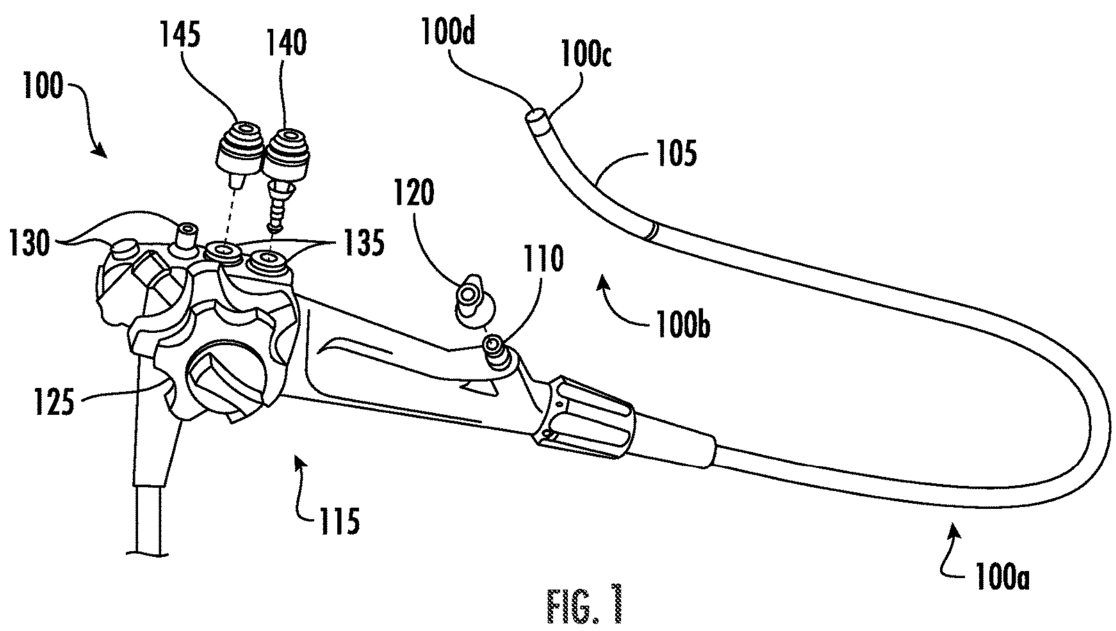
FIG. 1 depicts components of an endoscope.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

This disclosure is now described with reference to an exemplary medical system that may be used in endoscopic medical procedures. However, it should be noted that reference to this particular procedure is provided only for convenience and not intended to limit the disclosure. A person of ordinary skill in the art would recognize that the concepts underlying the disclosed devices and related methods of use may be utilized in any suitable procedure, medical or otherwise. This disclosure may be understood with reference to the following description and the appended drawings, the same or similar reference numbers will be used through the drawings to refer to the same or like parts.

The term "distal" refers to a portion farthest away from a user when introducing a device into a patient. By contrast, the term "proximal" refers to a portion closest to the user when placing the device into the patient. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." Further, as used herein, the terms "about," "approximately" and "substantially" indicate a range of values within +/−10% of a stated or implied value. Additionally, terms that indicate the geometric shape of a component/surface refer to exact and approximate shapes.

Embodiments of the present disclosure are described with specific reference to a bottle (e.g., container, reservoir, or the like) and tube assembly or set. It should be appreciated that such embodiments may be used to supply fluid and/or gas to an endoscope, for a variety of different purposes, including, for example, to facilitate insufflation of a patient, lens washing, and/or to irrigate a working channel to aid in flushing/suctioning debris during an endoscopic procedure.

Although the present disclosure includes descriptions of a container and tube set suitable for use with an endoscope system to supply fluid and/or gas to an endoscope, the devices, systems, and methods herein could be implemented in other medical systems requiring fluid and/or gas delivery, and for various other purposes.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Conventionally, endoscope devices have been widely used for performing diagnostic and/or therapeutic treatments. During endoscopic procedures, physicians may use a combination of air, irrigation and lens wash as a means of flushing debris, cleaning optics, and insufflating the working lumen. Some systems may use two separate water bottles for irrigation and lens wash while other systems may use a single water bottle for both irrigation and lens wash. As clinicians work through each case, some volume of water is depleted from the water bottle and bottles may need to be replaced one or more times over the course of the day. The process of exchanging bottles may require the user to bend or stoop down, remove the cap and associated inlet tubes from the empty bottle, and place them into a full bottle of sterile water without touching/contaminating the tubes against the external bottle or other non-sterile surfaces (e.g., so as not to create an infection risk to the patient). This may be especially difficult in the single bottle devices where multiple inlet hoses dangle from the cap when removing the cap to replace the sterile water bottle.

Figure 2:
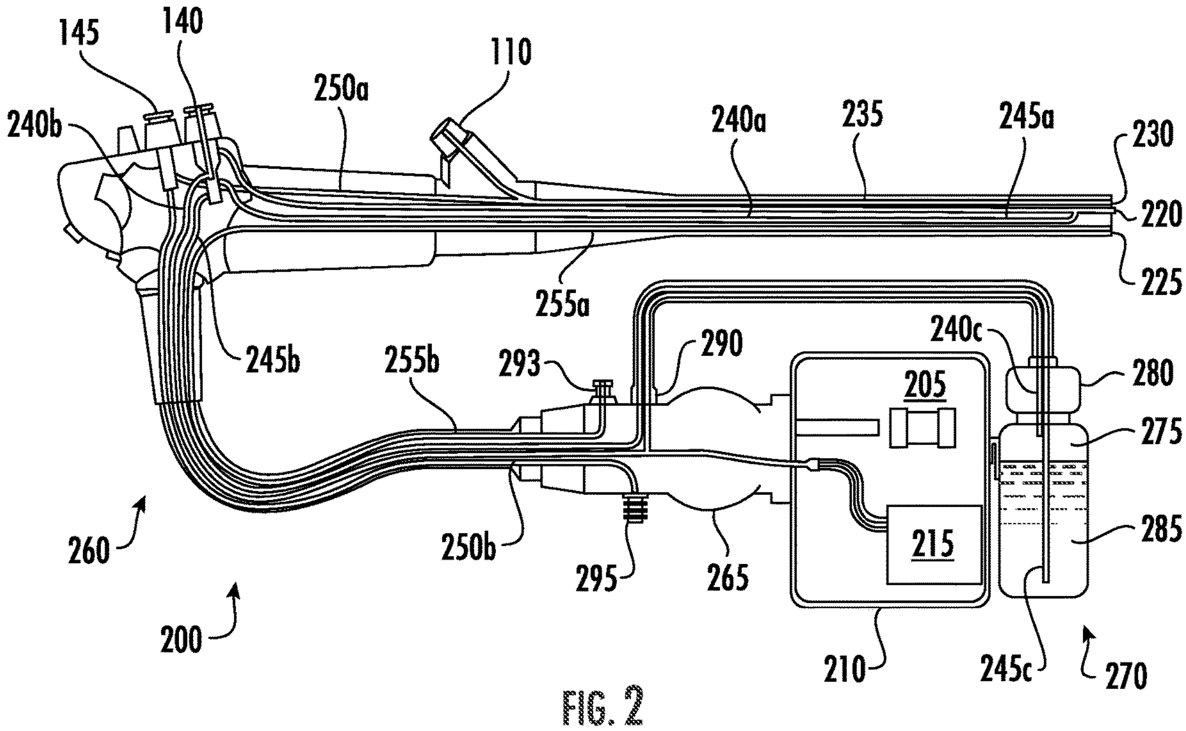
FIG. 2 depicts components of an endoscope system with endoscope, light source, light source connector, water reservoir, and tubing assembly for air and lens wash fluid delivery.

With reference to FIGS. 1-2, an exemplary endoscope 100 and system 200 are depicted that may comprise an elongated shaft 100*a* that is inserted into a patient. A light source 205 feeds illumination light to a distal portion 100*b* of the endoscope 100, which may house an imager (e.g., CCD or CMOS imager) (not shown). The light source 205 (e.g., lamp) is housed in a video processing unit 210 that processes signals that are input from the imager and outputs processed video signals to a video monitor (not shown) for viewing. The video processing unit 210 also serves as a component of an air/water feed circuit by housing a pressurizing pump 215, such as an air feed pump, in the unit.

The endoscope shaft 100*a* may include a distal tip 100*c* provided at the distal portion 100*b* of the shaft 100*a* and a flexible bending portion 105 proximal to the distal tip 100*c*. The flexible bending portion 105 may include an articulation joint (not shown) to assist with steering the distal tip 100*c*. On an end face 100*d* of the distal tip 100*c* of the endoscope 100 is a gas/lens wash nozzle 220 for supplying gas to insufflate the interior of the patient at the treatment area and for supplying water to wash a lens covering the imager. An irrigation opening 225 in the end face 100*d* supplies irrigation fluid to the treatment area of the patient. Illumination windows (not shown) that convey illumination light to the treatment area, and an opening 230 to a working channel 235 extending along the shaft 100*a* for passing tools to the treatment area, may also be included on the face 100*d* of the distal tip 100*c*. The working channel 235 extends along the shaft 100*a* to a proximal channel opening 110 positioned distal to an operating handle 115 of the endoscope 100. A biopsy valve 120 may be utilized to seal the channel opening 110 against unwanted fluid egress.

The operating handle 115 may be provided with knobs 125 for providing remote 4-way steering of the distal tip via wires connected to the articulation joint in the bendable flexible portion 105 (e.g., one knob controls up-down steering and another knob control for left-right steering). A plurality of video switches 130 for remotely operating the video processing unit 210 may be arranged on a proximal end side of the handle 115. In addition, the handle 115 is provided with dual valve wells 135. One of the valve wells 135 may receive a gas/water valve 140 for operating an insufflating gas and lens water feed operation. A gas supply line 240*a* and a lens wash supply line 245*a* run distally from the gas/water valve 140 along the shaft 100*a* and converge at the distal tip 100*c* proximal to the gas/wash nozzle 220 (FIG. 2). The other valve well 135 receives a suction valve 145 for operating a suction operation. A suction supply line 250*a* runs distally from the suction valve 145 along the shaft 100*a* to a junction point in fluid communication with the working channel 235 of the endoscope 100.

The operating handle 115 is electrically and fluidly connected to the video processing unit 210, via a flexible umbilical 260 and connector portion 265 extending therebetween. The flexible umbilical 260 has a gas (e.g., air or $CO_2$) feed line 240*b*, a lens wash feed line 245*b*, a suction feed line 250*b*, an irrigation feed line 255*b*, a light guide (not shown), and an electrical signal cable (not shown). The connector portion 265 when plugged into the video processing unit 210 connects the light source 205 in the video processing unit with the light guide. The light guide runs along the umbilical 260 and the length of the endoscope shaft 100*a* to transmit light to the distal tip 100*c* of the endoscope 100. The connector portion 265 when plugged into the video processing unit 210 also connects the air pump 215 to the gas feed line 240*b* in the umbilical 260.

A water reservoir or container 270 (e.g., water bottle) is fluidly connected to the endoscope 100 through the connector portion 265 and the umbilical 260. A length of gas supply tubing 240*c* passes from one end positioned in an air gap 275 between the top 280 (e.g., bottle cap) of the reservoir 270 and the remaining water 285 in the reservoir to a detachable gas/lens wash connection 290 on the outside of the connector portion 265. The detachable gas/lens wash connection 290 may be detachable from the connector portion 265 and/or the gas supply tubing 240*c*. The gas feed line 240*b* from the umbilical 260 branches in the connector portion 265 to fluidly communicate with the gas supply tubing 240*c* at the detachable gas/lens wash connection 290, as well as the air pump 215. A length of lens wash supply tubing 245*c*, with one end positioned at the bottom of the reservoir 270, passes through the top 280 of the reservoir 270 to the same detachable connection 290 as the gas supply tubing 240*c* on the connector portion 265. In other embodiments, the connections may be separate and/or separated from each other. The connector portion 265 also has a detachable irrigation connection 293 for irrigation supply tubing (not shown) running from a source of irrigation water (not shown) to the irrigation feed line 255*b* in the umbilical 260. The detachable irrigation connection 293 may be detachable from the connector portion 265 and/or the irrigation supply tubing (not shown). In some embodiments, irrigation water is supplied via a pump (e.g., peristaltic pump) from a water source independent (not shown) from the water reservoir 270. In other embodiments, the irrigation supply tubing and lens wash supply tubing 245*c* may source water from the same reservoir. The connector portion 265 may also include a detachable suction connection 295 for suction feed line 250*b* and suction supply line 250*a* fluidly connecting a vacuum source (e.g., hospital house suction) (not shown) to the umbilical 260 and endoscope 100. The detachable suction connection 295 may be detachable from the connector portion 265 and/or the suction feed line 250*b* and/or the vacuum source.

The gas feed line 240*b* and lens wash feed line 245*b* are fluidly connected to the valve well 135 for the gas/water valve 140 and configured such that operation of the gas/water valve 140 in the well controls supply of gas or lens wash to the distal tip 100*c* of the endoscope 100. The suction feed line 250*b* is fluidly connected to the valve well 135 for the suction valve 145 and configured such that operation of the suction valve in the well controls suction applied to the working channel 235 of the endoscope 100.

Referring to FIG. 2, an exemplary operation of an endoscopic system 200, including an endoscope such as endoscope 100 above, is explained. Air from the air pump 215 in the video processing unit 210 is flowed through the connector portion 265 and branched to the gas/water valve 140 on the operating handle 115 through the gas feed line 240*b* in the umbilical 260, as well as through the gas supply tubing 240*c* to the water reservoir 270 via the connection 290 on the connector portion 265. When the gas/water valve 140 is in a neutral position, without the user's finger on the valve, air is allowed to flow out of the valve to atmosphere. In a first position, the user's finger is used to block the vent to atmosphere. Gas is allowed to flow from the valve 140 down the gas supply line 240*a* and out the distal tip 100*c* of the endoscope 100 in order to, for example, insufflate the treatment area of the patient. When the gas/water valve 140 is pressed downward to a second position, gas is blocked from exiting the valve, allowing pressure of the air passing from the air pump 215 to rise in the water reservoir 270. Pressurizing the water source forces water out of the lens wash supply tubing 245*c*, through the connector portion 265, umbilical 260, through the gas/water valve 140 and down the lens wash supply line 245*a*, converging with the gas supply line 240*a* prior to exiting the distal tip 100*c* of the endoscope 100 via the gas/lens wash nozzle 220. Air pump pressure may be calibrated to provide lens wash water at a relatively low flow rate compared to the supply of irrigation water.

The volume of the flow rate of the lens wash is governed by gas pressure in the water reservoir 270. When gas pressure begins to drop in the water reservoir 270, as water is pushed out of the reservoir 270 through the lens wash supply tubing 245*c*, the air pump 215 replaces lost air supply in the reservoir 270 to maintain a substantially constant pressure, which in turn provides for a substantially constant lens wash flow rate. In some embodiments, a filter (not shown) may be placed in the path of the gas supply tubing 240*c* to filter-out undesired contaminants or particulates from passing into the water reservoir 270. In some embodiments, outflow check valves or other one-way valve configurations (not shown) may be placed in the path of the lens wash supply tubing to help prevent water from back-flowing into the reservoir 270 after the water has passed the valve.

A relatively higher flow rate of irrigation water is typically required compared to lens wash, since a primary use is to clear the treatment area in the patient of debris that obstructs the user's field of view. Irrigation is typically achieved with the use of a pump (e.g., peristaltic pump), as described. In embodiments with an independent water source for irrigation, tubing placed in the bottom of a water source is passed through the top of the water source and threaded through the head on the upstream side of the pump. Tubing on the downstream side of the pump is connected to the irrigation feed line 255*b* in the umbilical 260 and the irrigation supply line 255*a* endoscope 100 via the irrigation connection 293 on the connector portion 265. When irrigation water is required, fluid is pumped from the water source by operating the irrigation pump, such as by depressing a footswitch (not shown), and flows through the irrigation connection 293, through the irrigation feed line 255*b* in the umbilical, and down the irrigation supply line in the shaft 100*a* of the endoscope to the distal tip 100*c*. In order to equalize the pressure in the water source as water is pumped out of the irrigation supply tubing, an air vent (not shown) may be included in the top 280 of the water reservoir 270. The vent allows atmospheric air into the water source preventing negative pressure build-up in the water source, which could create a vacuum that suctions undesired matter from the patient back through the endoscope toward the water source. In some embodiments, outflow check valves or other one-way valve configurations (not shown), similar to the lens wash supply tubing 245*c*, may be placed in the path of the irrigation supply tubing to help prevent backflow into the reservoir after water has passed the valve. In some cases, irrigation water may be supplied from the water reservoir 270. Some illustrative systems where the supply tubing for irrigation and lens wash are connected to and drawn from a single water reservoir are described in commonly assigned U.S. patent application Ser. No. 17/558,239, titled INTEGRATED CONTAINER AND TUBE SET FOR FLUID DELIVERY WITH AN ENDOSCOPE and U.S. patent application Ser. No. 17/558,256, titled TUBING ASSEMBLIES AND METHODS FOR FLUID DELIVERY, the disclosures of which are hereby incorporated by reference.

Figure 3:
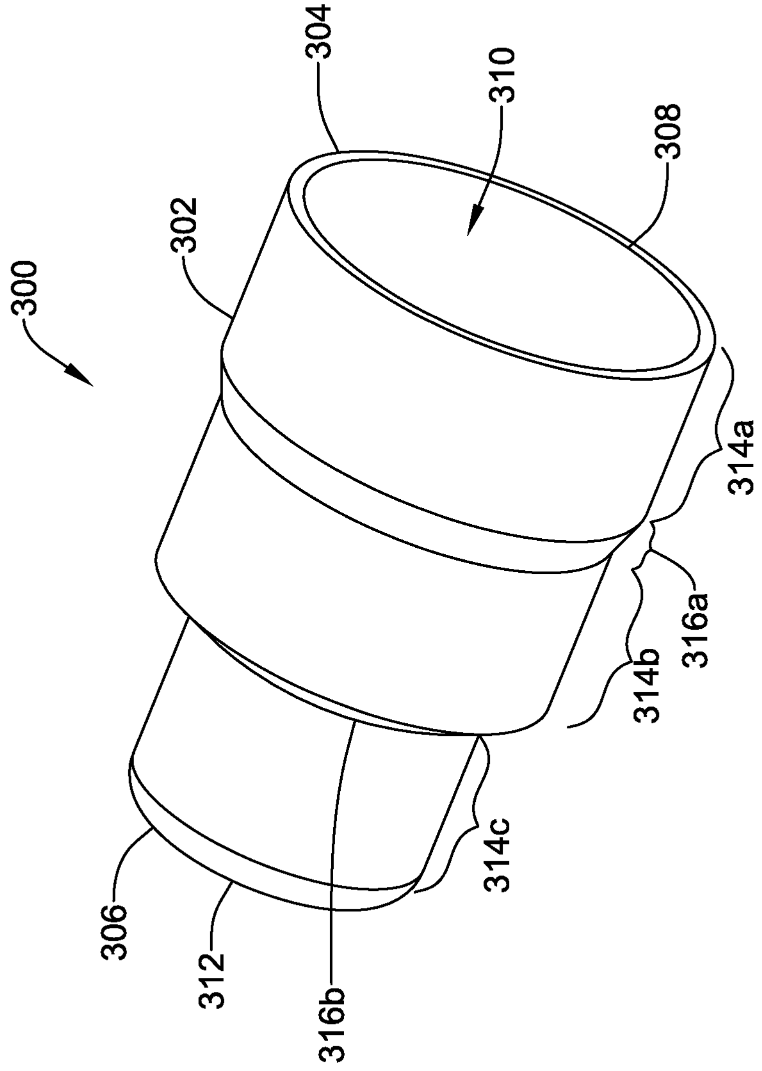
FIG. 3 depicts a perspective view of an illustrative cap configured to be secured to an endoscope end of a water supply tubing.

In some cases, it may be desirable to prevent water/fluid from leaking out of the gas/lens wash supply tubing 240*c*, 245*c* (e.g., configured to be connected to gas/lens wash connector 290) and/or the irrigation tubing (not explicitly shown) (e.g., configured to be connected to the irrigation connector 293). While the illustrative caps are described with respect to the gas/lens wash supply tubing 240*c*, 245*c*, it should be understood that the connectors and coupling configurations described herein may be used at other connection points, as desired. FIG. 3 depicts a perspective view of an illustrative cap 300 configured to be secured to an endoscope end of the gas/lens wash supply tubing 240*c*, 245*c*.

The cap 300 may include a body or housing 302 extending from a first end 304 to a second end 306. The first end 304 may define an opening or aperture 308 in communication with an internal cavity 310 of the housing 302. The second end 306 may include an end cap or wall 312 such that the cavity 310 does not extend through an entire length of the cap 300. A diameter of the cap 300 may vary from the first end 304 to the second end 306. For example, the outer diameter of the cap 300 may decrease in diameter from the first end 304 to the second end 306. In some cases, the change in diameter may occur in an abrupt, stair-step manner. In other examples, the change in diameter may be gradual or sloped. In yet other examples, the cap 300 may include both abrupt and gradual changes in diameter. In the illustrated embodiment, the cap 300 may include a first region 314*a* having a first generally uniform outer and a first generally uniform inner diameter, a second region 314*b* having a second generally uniform outer and a second generally uniform inner diameter, and a third region 314*c* having a third generally uniform outer and a third generally uniform inner diameter. The first region 314*a* may have a greater outer/inner diameter than the second region 314*b* and the second region 314*b* may have a greater outer/inner diameter than the third region 314*c*. The cap 300 may further include a first transition region 316*a* between the first region 314*a* and the second region 314*b*. The first transition region 316*a* may be sloped or tapered to gradually transition from the first inner/outer diameter to the second outer/inner diameter. However, this is not required. In some embodiments, the first transition region 316*a* may be abrupt or a stair-step transition. The cap 300 may further include a second transition region 316*b* between the second region 314*b* and the third region 314*c*. The second transition region 316*b* may be sloped or tapered to gradually transition from the first inner/outer diameter to the second outer/inner diameter. However, this is not required. In some embodiments, the second transition region 316*b* may be abrupt or a stair-step transition. It is contemplated that the wall thickness of the cap 300 may remain substantially constant from the first end 304 to the second end 306 such that the inner diameter of the cap 300 varies in a similar manner to the outer diameter. In some examples, the inner and outer diameter of the cap 300 may be formed to mirror an outer diameter of the endoscope end of the gas/lens wash supply tubing 240*c*, 245*c*.

Figure 4:
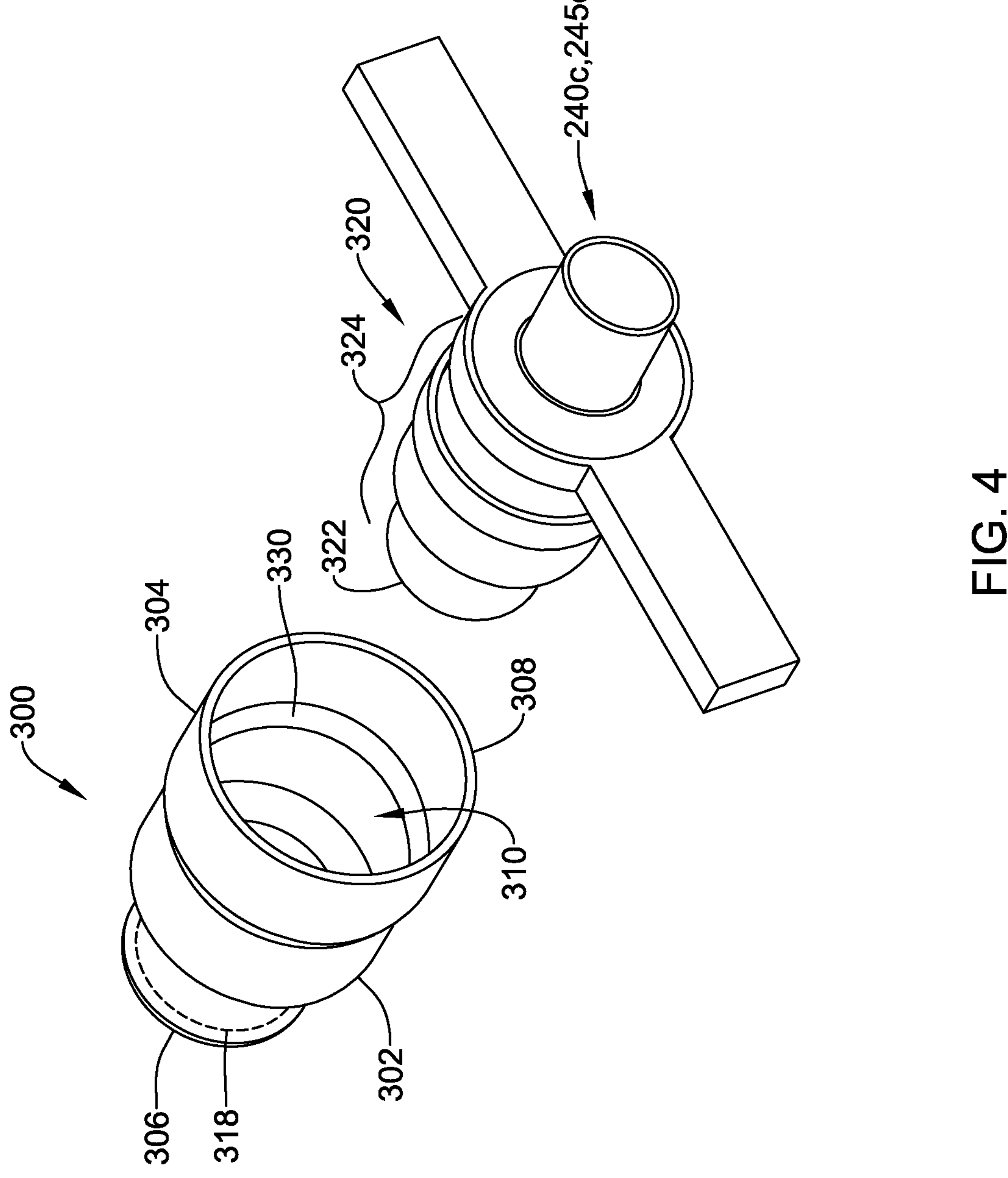
FIG. 4 depicts a perspective view of the illustrative cap of FIG. 3 with the endoscope end of a gas/lens wash supply tubing.

FIG. 4 depicts a perspective view of the illustrative cap 300 with the endoscope end 320 of the gas/lens wash supply tubing 240*c*, 245*c*. The cap 300 may be coupled with the endoscope end 320 of the gas/lens wash supply tube 240*c*, 245*c* by placing the cap 300 over the endoscope end 320 such that the endoscope end 320 is disposed within the cavity 310. It is contemplated that the cap 300 may be releasably secured to the endoscope end 320 through a snap fit, a friction fit, a threaded engagement, quick release mechanisms (e.g., a bayonet-style locking mechanism), or other releasable coupling mechanism. In some examples, the releasable coupling mechanism used to secure the cap 300 to the endoscope end 320 may be determined by the type of coupling mechanism used to couple to the endoscope end 320 to the endoscope (e.g., different brands of endoscopes may incorporate different connection types for coupling the gas/lens wash supply tubing 240*c*, 245*c* to the endoscope). For example, the cap 300 may be provided with internal threading, external threading, Luer-style fittings, etc. It is further contemplated that a shape of the cap 300 may be determined by the type of coupling mechanism used to couple to the endoscope end 320 to the endoscope.

When the endoscope end 320 of the gas/lens wash supply tube 240*c*, 245*c* is inserted into the cavity 310 of the cap 300, the open end 322 of the gas/lens wash supply tube 240*c*, 245*c* may contact the wall 312 of the second end 306 of the cap 300 to form a fluid tight seal between the endoscope end 320 and the cap 300. This may prevent water from leaking from the open end 322 of the gas/lens wash supply tube 240*c*, 245*c* when the gas/lens wash supply tube 240*c*, 245*c* is uncoupled from the endoscope regardless of a positioning of the gas/lens wash supply tube 240*c*, 245*c*. In some examples, a sealing member, such as, but not limited to a deformable insert 318 may be within the cavity 310 against the wall 312 to help provide a fluid tight seal. Additionally, or alternatively, one or more O-rings or gaskets 330 may be positioned within the cavity 310 to help maintain the connection between the cap 300 and the endoscope end 320 of the gas/lens wash supply tube 240*c*, 245*c*. In an illustrative example, one or more O-rings or gaskets 330 may be positioned adjacent to one or more of the transition regions 316*a*-*b*. However, the O-rings or gaskets 330 may be located at other positions within the cap 300, as desired. The cap 300 may be sized and shaped such that the cap 300 is disposed over the connection region 324 of the endoscope end 320 of the gas/lens wash supply tube 240*c*, 245*c*. Positioning the connection region 324 of the endoscope end 320 within the cavity 310 of the cap 300 may prevent the connection region 324 from contacting surfaces when the gas/lens wash supply tube 240*c*, 245*c* is not coupled to an endoscope which may help prevent contamination of the endoscope end 320 of the gas/lens wash supply tube 240*c*, 245*c* thus helping achieve infection prevention.

While the cap 300 has been shown and described as fitting over an outer surface of the endoscope end 320 of the gas/lens wash supply tube 240*c*, 245*c*, in some examples, the cap 300 may be inserted into a lumen of the endoscope end 320 of the gas/lens wash supply tube 240*c*, 245*c*. For example, the cap 300 may function as a plug that is inserted into the endoscope end 320 of the gas/lens wash supply tube 240*c*, 245*c* as opposed to over an outer surface thereof. In some cases, the cap 300 may include a portion configured to be disposed within the endoscope end 320 of the gas/lens wash supply tube 240*c*, 245*c* and a portion that extends over an outer surface thereof for infection prevention.

Figure 5:
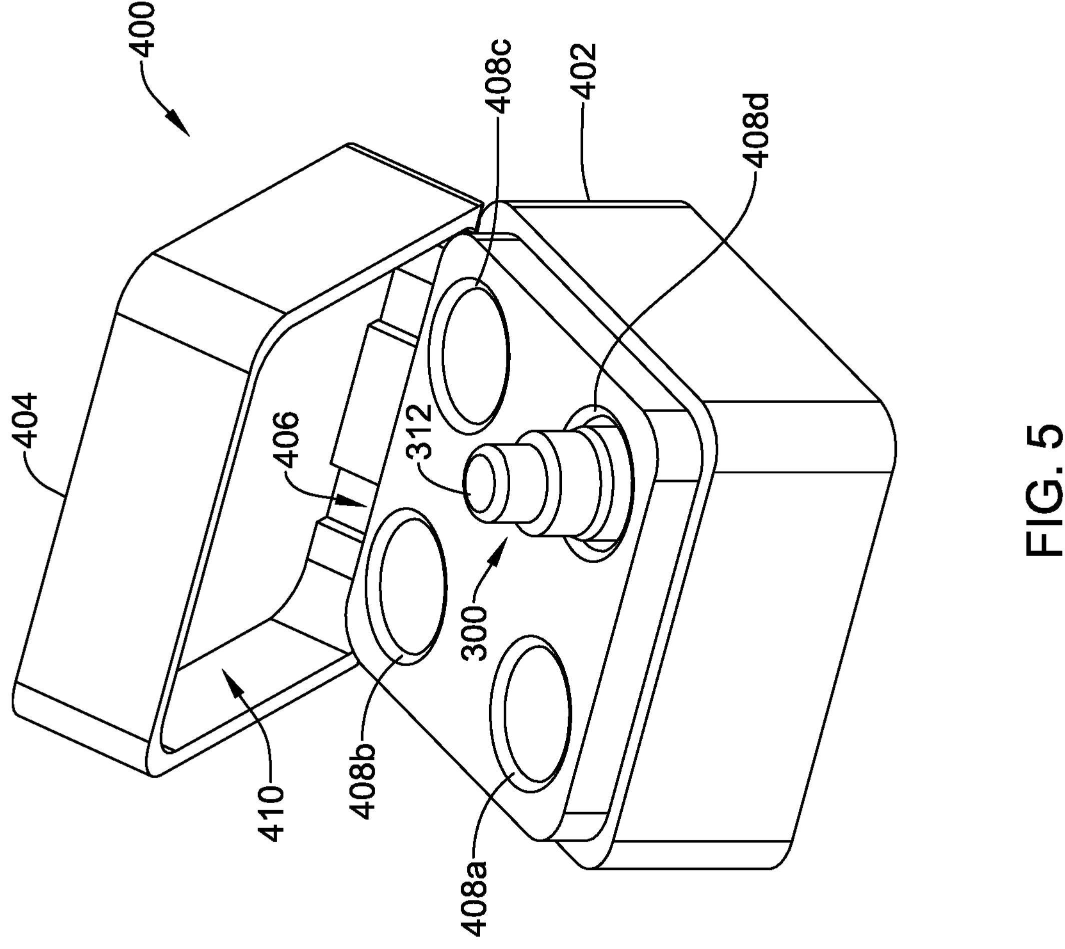
FIG. 5 depicts a perspective view of an illustrative storage case in an open configuration and having an illustrative cap positioned therein.

In some examples, the cap 300 may be tethered to the gas/lens wash supply tube 240*c*, 245*c* such that when the cap 300 is not in use, the cap 300 remains in close proximity to the gas/lens wash supply tube 240*c*, 245*c*. In other examples, when the cap 300 is not in use (e.g., when the endoscope end 320 is coupled to an endoscope), the cap 300 may be manually removed from the connection region 324 and placed in a storage case. FIG. 5 depicts a perspective view of an illustrative storage case 400 in an open configuration and having an illustrative cap 300 positioned therein. The storage case 400 may include a base 402 and a lid 404. While the storage case 400 is illustrated as having a generally cubic or rectangular prism shape, the storage case 400 may take any shape desired. The storage case 400 may be formed from a rigid material, such as, but not limited to, acrylonitrile butadiene styrene terpolymer (ABS), thermoplastics, other polymers, hard rubber, metals, alloys, etc. Other examples, however, may include storage cases 400 made from a flexible or semi-rigid material, such as a flexible or semi-rigid polymeric material.

The lid 404 may be coupled to the base 402 in an orientation to cover the base 402 in a closed configuration (not explicitly shown). The lid 404 and base 402 may have identical or substantially the same outer dimensions to provide a uniform outer surface. In other examples, the lid 404 may have outer dimensions larger or smaller than the base 402. The lid 404 may be pivotably coupled to the base 402 at a hinge assembly 406. The hinge assembly 406 may include pins extending from the lid 404 into apertures in the base 402. However, other hinge assemblies and configurations may be used as desired. The lid 404 may be rotated between a closed configuration and an open configuration (as shown in FIG. 5). In some examples, the base 402 and lid 404 may include features to selectively and reversibly couple the lid 404 to the base 402. Some illustrative coupling features may include, but are not limited to, a magnetic closure, snap fit, friction fit, or other suitable coupling mechanism. While not explicitly shown, the base 402 and/or lid 404 may include a include a cut-out portion or recess on the front to provide a space for the user to grasp the lid 404 and rotate the lid 404 away from the base 402.

The base 402 may include a plurality of cavities or wells 408*a-d* configured to receive one or more caps 300. Each well 408*a-d* may be configured to receive a single cap 300. For example, a cap 300 is disposed within one of the wells 408*d*. In some examples, the wells 408*a-d* may each be of the same general shape and size to each receive a cap 300 of a similar shape and size. In other examples, the wells 408*a-d* may be of differing shapes and/or sizes to receive caps of differing shapes and sizes. For example, the wells 408*a-d* may be sized and shaped to receive a plurality of different caps 300. It is contemplated that caps 300 of different sizes and shapes may be provided to accommodate differing endoscope ends 320 of the gas/lens wash supply tube 240*c*, 245*c*. The base 402 may include fewer than four or more than four wells 408*a-d*, as desired.

The lid 404 may include a recess or cavity 410 configured to receive a second end region of the cap 300. For examples, the cap 300 may protrude from the well 408*d* to allow a user to easily grip the cap 300 adjacent the second end 306 thereof. The cavity 410 of the lid 404 may be sized and shaped to accommodate this portion of the cap 300 while allowing the lid 404 to close over the base 402.

Figure 6:
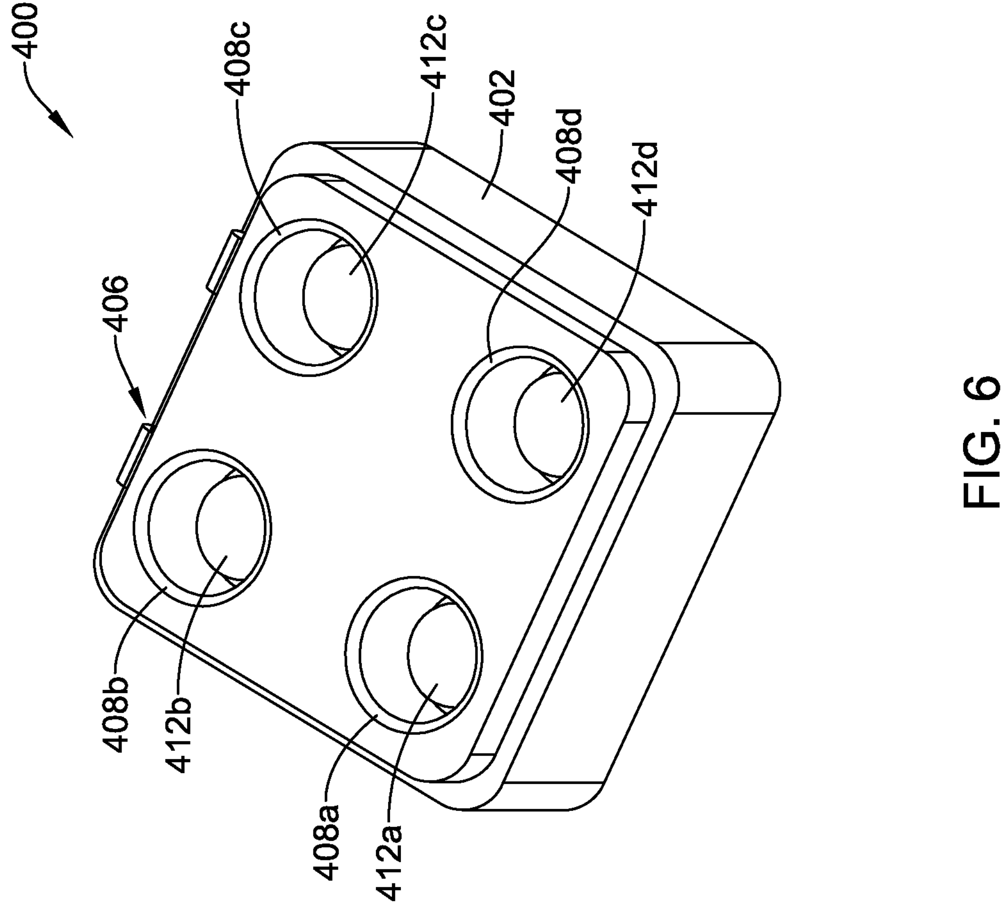
FIG. 6 depicts a perspective view of the illustrative base of the storage case of FIG. 5.

Referring additionally to FIG. 6 which depicts a perspective view of the illustrative base 402 of the storage case 400, each well 408*a-d* may include an insert or seat 412*a-d* disposed therein. The insert 412*a-d* may be formed from a perforated foam, such as, but not limited to, a polyethylene foam. However, other materials including, but not limited to, other polymeric materials, may be used as desired. In some cases, an antibacterial or bacteriostatic material may be infused into the insert 412*a-d* to provide additional antimicrobial properties. Some illustrative antibacterial or bacteriostatic materials may include, but are not limited to, ionized silver, copper, zinc, quaternary ammonia compounds, etc. The inserts 412*a-d* may be soaked in an antiseptic liquid which may help in sanitizing the cap 300. In some cases, the inserts 412*a-d* may be soaked in an antiseptic liquid prior to being disposed within the wells 408*a-d*. In other cases, the antiseptic liquid may be poured into the wells 408-*ad* to soak the inserts 412*a-d*. In some examples, the inserts 412*a-d* may have a diameter that is similar to an inner diameter of the first region 314*a* so that the inner diameter of the first region 314*a* contacts an outer edge of the insert 412*a-d*. However, this is not required. While the inserts 412*a-d* are illustrated as having a generally disc-like shape, the inserts 412*a-d* may be taken other shapes as desired. In some embodiments, the insert 412*a-d* may be configured to contact an inner surface of the cap 300. For example, the insert 412*a-d* may be sized and shaped to conform to an entire inner surface, or a portion thereof, of the cavity 310 of the cap 300 such that the antiseptic fluid may contact (and disinfect) the surfaces of the cap 300 that may contact the surfaces of the endoscope end 320 of the gas/lens wash supply tube 240*c*, 245*c*.

Figure 7:
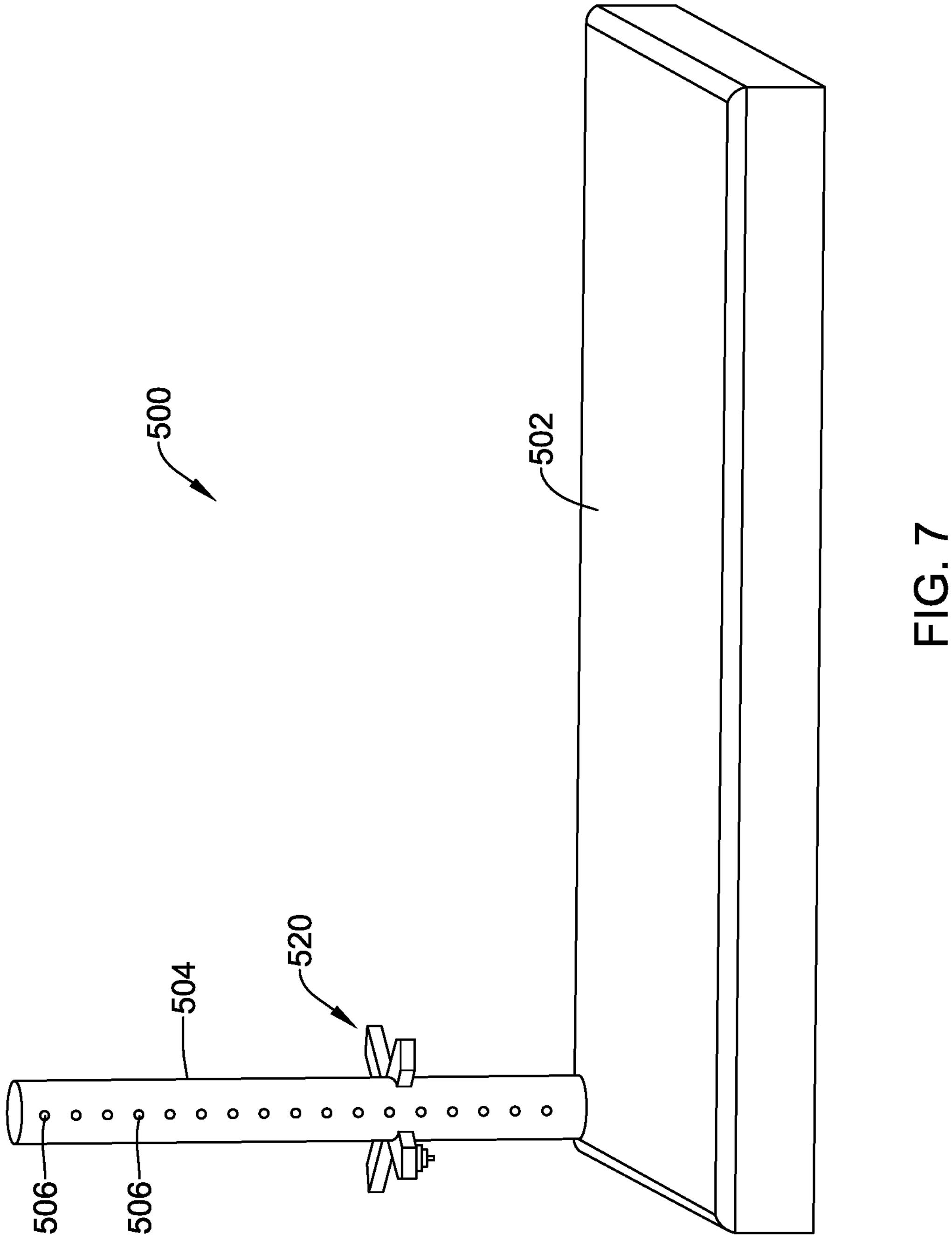
FIG. 7 depicts a schematic view of a portion of an illustrative endoscope tower including a clamp for securing a gas/lens wash supply tube or other fluid supply tube.

In some cases, it may be desirable to secure the endoscope end of the gas/lens wash supply tube 240*c*, 245*c* to the endoscope tower to prevent water from leaking from the endoscope end of the gas/lens wash supply tube 240*c*, 245*c* and to prevent the endoscope end of the gas/lens wash supply tube 240*c*, 245*c* from contacting the floor or other surfaces which may contaminate the gas/lens wash supply tube 240*c*, 245*c*. FIG. 7 depicts a schematic view of a portion of an illustrative endoscope tower 500 including a clamp 520 for securing a gas/lens wash supply tube 240*c*, 245*c* when it is not in use. Generally, the endoscope tower 500 may include a shelf portion 502 and one or more posts 504. While not explicitly shown, the endoscope tower 500 may include additional features. For example, the endoscope tower 500 be elevated off the ground on a rolling cart and/or include additional shelves, posts, etc. The post 504 may include a plurality of pin holes 506 for adjusting the positioning of various pieces of equipment that are coupled to the post 504. For example, monitors or other pieces or equipment may be adjustably secured to the post 504 using a pin. A removable clamp 520 may be secured to the post 504 for securing the gas/lens wash supply tube 240*c*, 245*c* thereto.

Figure 8:
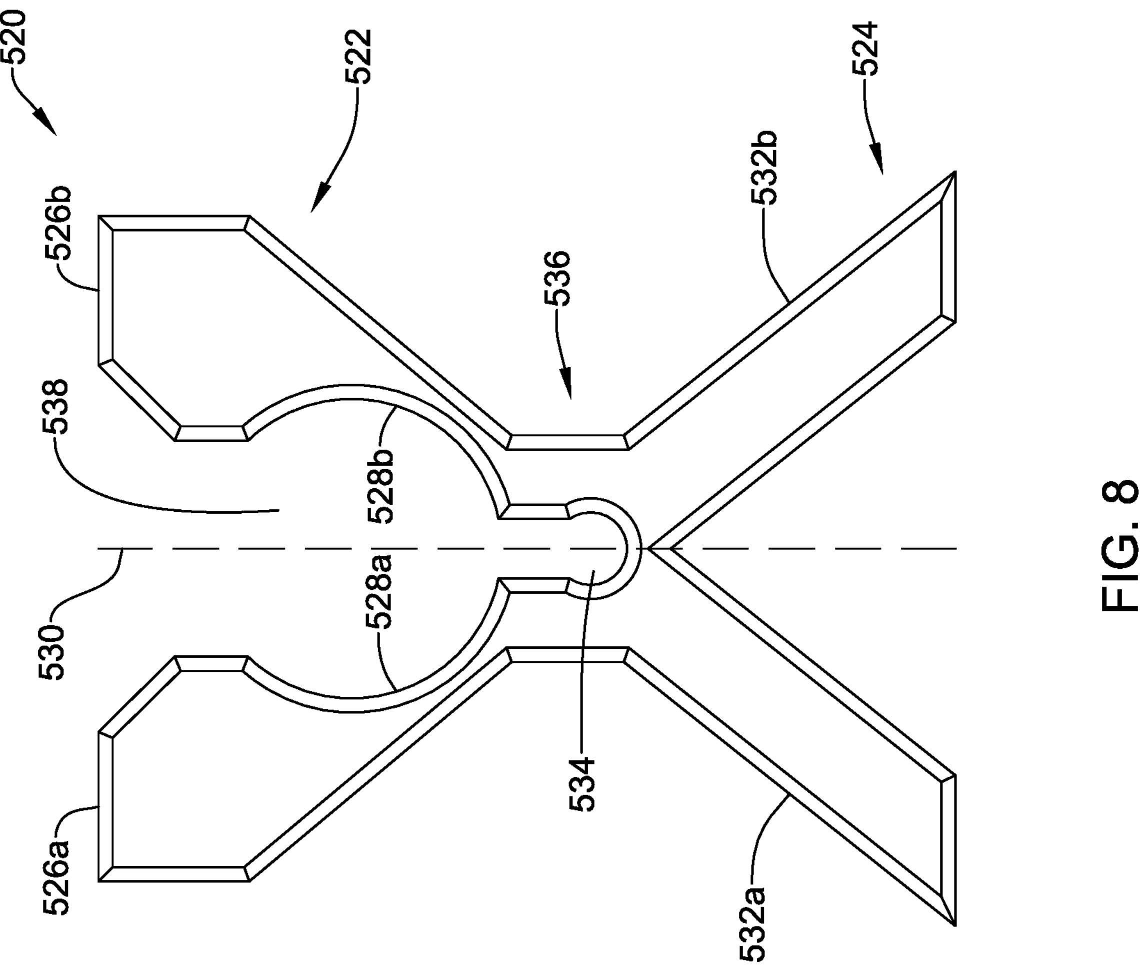
FIG. 8 depicts a top view of the illustrative clamp of FIG. 7.

Referring additionally to FIG. 8, which depicts a top view of the illustrative clamp 520, the clamp 520 may include a securing region 522 configured to grip the post 504 and an actuation region 524 configured to be actuated to selectively expand the securing region 522. The securing region 522 may include a first arm 526*a* and a second arm 526*b* spaced a distance from the first arm 526*a*. Each arm 526*a-b* may include a curved inner surface 528*a-b* configured to conform to an outer surface of the post 504. In the absence of an applied force, the arms 526*a-b* may be biased inwards towards a central axis 530 of the clamp 520 such that the curved inner surfaces 528*a-b* grip the post 504 when the clamp 520 is attached thereto. The actuation region 524 may include a first arm 532*a* and a second arm 532*b*. Collectively, the arms 526*a-b* of the securing region 522 and the arms 532*a-b* of the actuation region 524 may be angled or positioned such that the clamp 520 has a generally "X" shape. The clamp 520 may include a cut-out region 534 at an intersection region of the 526*a-b* of the securing region 522 and the arms 532*a-b* of the actuation region 524. The cut-out region 534 may be sized and shaped such that the arms 526*a-b* of the securing region 522 may move towards or away from the central axis 530. Further, the cut-out region

534 may be sized and shaped such that the arms 532*a-b* of the actuation region 524 may move towards the central axis 530 under an applied force.

The clamp 520 may be secured to the post 504 by exerting a squeezing force on the arms 532*a-b* of the actuation region 524 to move the arms 532*a-b* towards the central axis 530. As the arms 532*a-b* of the actuation region 524 move inwards, the arms 526*a-b* of the securing region 522 are deflected or moved outwards away from the central axis 530. While the arms 526*a-b* of the securing region 522 are deflected outwards the user may position the arms 526*a-b* of the securing region 522 about the post 504 and release the actuation region 524. When the arms 532*a-b* of the actuation region 524 are released, the arms 526*a-b* of the securing region 522 move towards the central axis 530 such that the curved surfaces 528*a-b* grip the post 504. In some cases, the curved surfaces 528*a-b* may include a textured surface or may be formed from a material that helps maintain the clamp 520 at the desired height. It is contemplated that a diameter of the post 504 may be greater than the space 538 between the curved surfaces 528*a-b* so that the curved surfaces 528*a-b* exert a force on the post 504.

Figure 9:
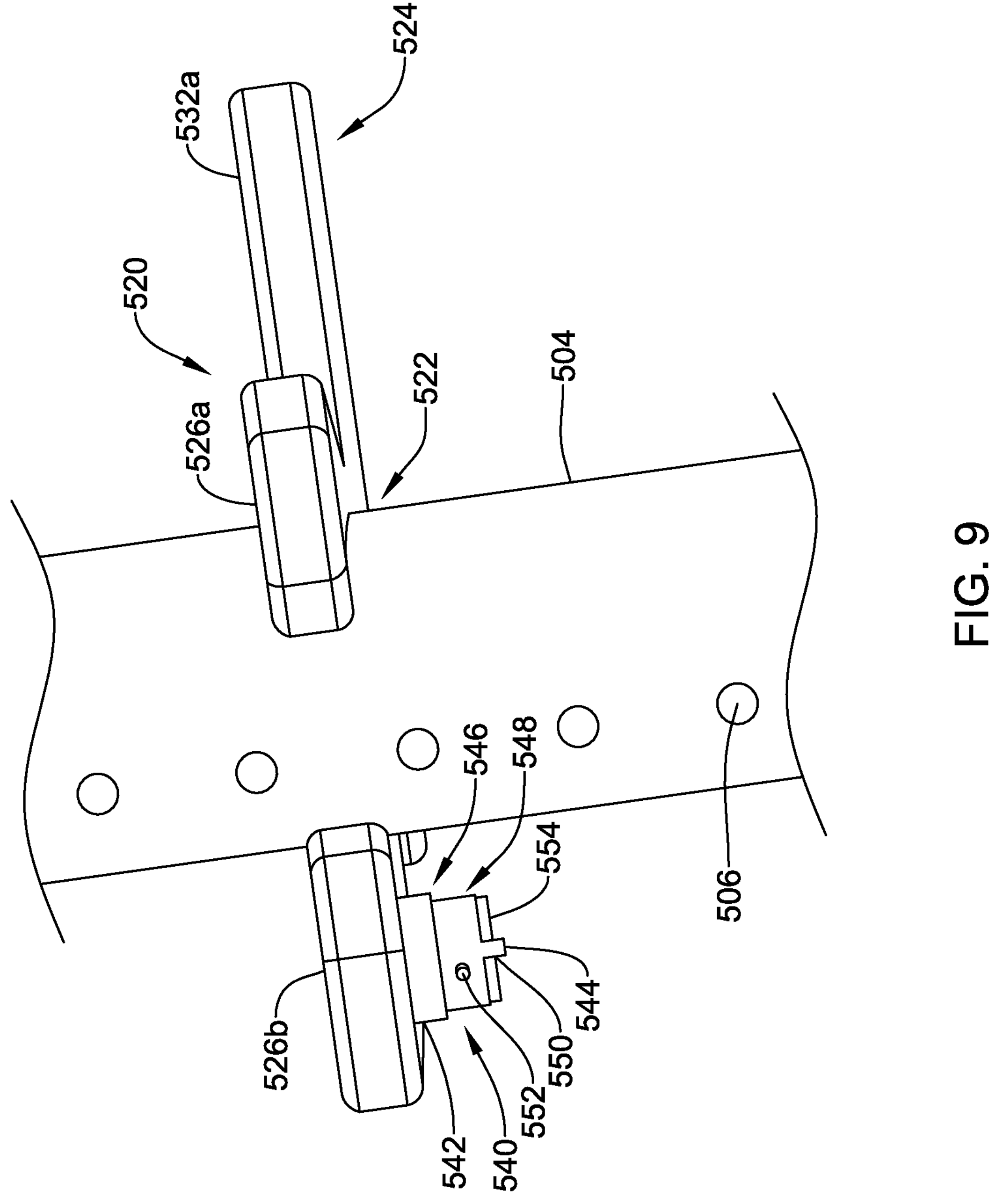
FIG. 9 depicts an enlarged perspective view of the illustrative clamp of FIG. 8 assembled with the post of FIG. 7.

FIG. 9 depicts an enlarged perspective view of the illustrative clamp 520 assembled with the post 504. The clamp 520 may further include a cap 540 extending from a bottom surface thereof. It is contemplated that the cap 540 may be formed as a single monolithic structure with the clamp 520 or may be formed as a separate component and subsequently coupled to the clamp 520. For example, cap 540 may be fixedly secured to the clamp 520 using, for example, an adhesive, welding, brazing, etc. or the cap 540 may be releasably secured to the clamp 520 using, for example, magnets, threaded arrangements, friction fits, etc.

The cap 540 may extend from a first end 542 coupled to the clamp 520 to a second end 544 configured to extend into the endoscope end of the gas/lens wash supply tube 240*c*, 245*c*. The cap 540 may have an outer diameter or outer cross-sectional dimension that varies along a length thereof. For example, a first end region 546 may have a first outer diameter, an intermediate region 548 may have a second outer diameter smaller than the first outer diameter, and a second end region 550 may have a third outer diameter smaller than the second outer diameter. It is contemplated that the outer profile of the cap 540 may mirror the inner profile of the endoscope end of the gas/lens wash supply tube 240*c*, 245*c*. It is contemplated that the intermediate region 548 and the second end region 550 may be configured to extend, at least partially, into the endoscope end of the gas/lens wash supply tube 240*c*, 245*c* while the first end region 546 may abut an end surface of the endoscope end of the gas/lens wash supply tube 240*c*, 245*c*.

The cap 540 may further include a coupling mechanism 552 positioned on/in the intermediate region 548. In the illustrated embodiment, the coupling mechanism 552 may be a pin extending radially outwards from the intermediate region 548 and configured to engage a Luer-style coupling mechanism on the endoscope end of the gas/lens wash supply tube 240*c*, 245*c*. However, other coupling mechanisms may be used, as desired. Other coupling mechanisms may include, but are not limited to, internal threading, external threading, snap fits, friction fits, etc. It is contemplated that the coupling mechanism 552 may be determined by the type of coupling mechanism on the endoscope end of the gas/lens wash supply tube 240*c*, 245*c*. Similarly, the outer (and/or inner) profile of the cap 540 may be determined, at least in part, by the type of coupling mechanism on the endoscope end of the gas/lens wash supply tube 240*c*, 245*c*. For example, in some examples, the cap 540 may be configured to be disposed over the endoscope end of the gas/lens wash supply tube 24*c*, 245*c* in a manner similar to that shown and described with respect to FIGS. 3-4 or FIGS. 11A-B (discussed below). While not explicitly shown, in some examples, the clamp 520 may include more than one type of cap or different caps such that a same clamp 520 may be used to secure more than one type of endoscope end of the gas/lens wash supply tube 240*c*, 245*c*. For example, a cap similar to that shown and described with respect to FIGS. 3-4 or FIGS. 11A-B, or caps of other designs, may be fixedly or releasably coupled to the clamp 520.

The cap 540 may further include an O-ring, gasket, or other sealing member 554. The sealing member 554 may be positioned anywhere along a length of the cap 540 to provide a fluid tight seal between the cap 540 and the endoscope end of the gas/lens wash supply tube 240*c*, 245*c*. In the illustrated embodiment, the sealing member 554 may be positioned adjacent a second end of the intermediate region 548. However, this is not required. In some cases, the cap 540 may include an embedded antibacterial, bacteriostatic, or anti-microbial material, although this is not required. Some illustrative antibacterial, bacteriostatic, or anti-microbial materials may include, but are not limited to, ionized silver, copper, zinc, quaternary ammonia compounds, etc.

Figure 10:
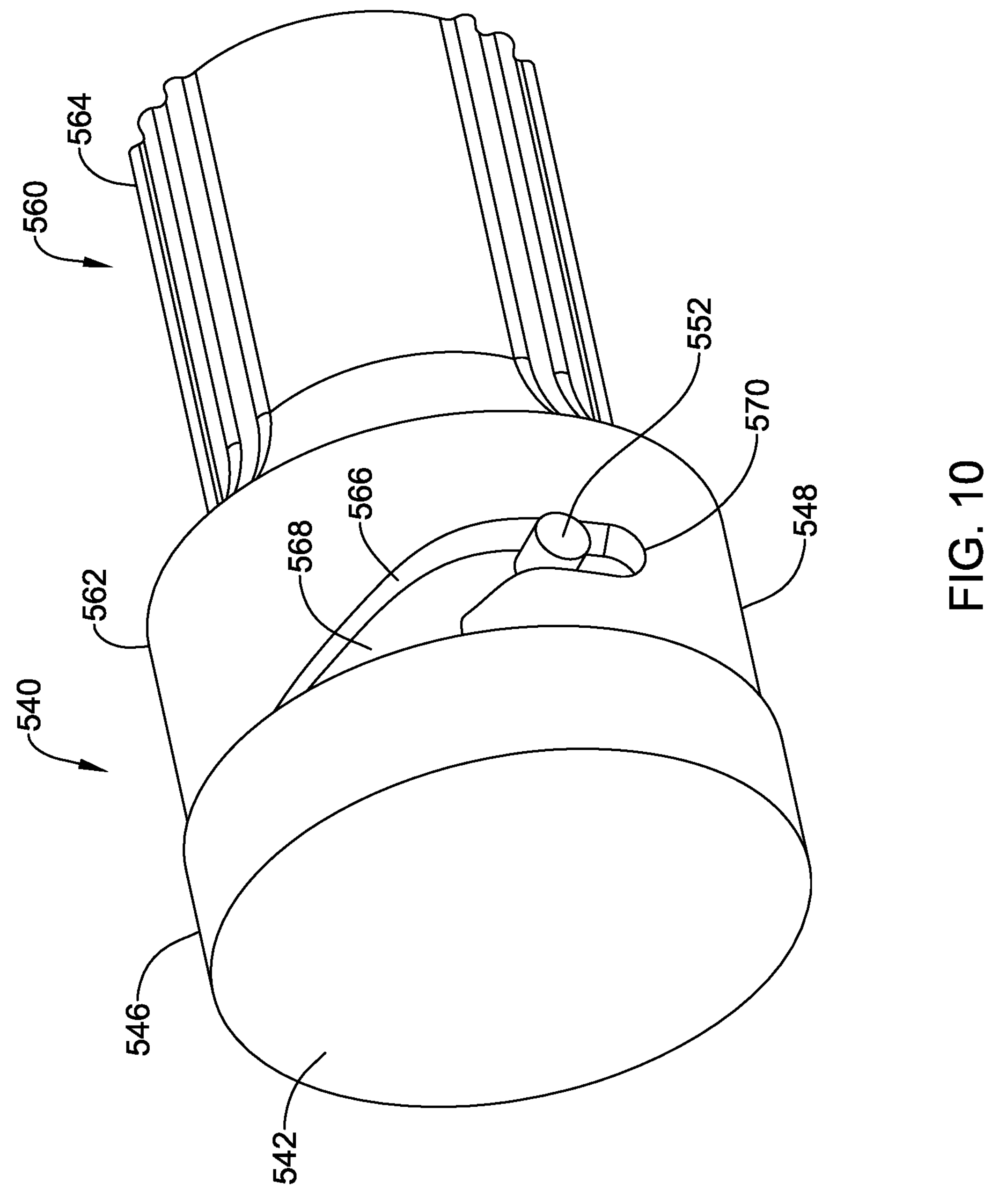
FIG. 10 depicts a perspective view of the illustrative cap of FIG. 9 coupled with another endoscope end of a gas/lens wash supply tube.

FIG. 10 depicts a perspective view of the illustrative cap 540 of FIG. 9 coupled with another endoscope end 560 of a gas/lens wash supply tube 240*c*, 245*c*. While the cap 540 is shown as separate from the clamp 520, it should be understood that the cap 540 may be fixedly or releasably coupled to the clamp 520. The endoscope end 560 of the gas/lens wash supply tube 240*c*, 245*c* may extend from a first end region 562 configured to be coupled to the endoscope and a second end region 564 configured to be coupled to the gas/lens wash supply tube 240*c*, 245*c*. As described above, the endoscope end 560 of the gas/lens wash supply tube 240*c*, 245*c* may have varying coupling mechanisms depending on the manufacturer and/or model of the endoscope. In the illustrated embodiment, the endoscope end 560 may have a Luer-style connection including a curved slot 566 extending from an open first end 568 to a closed second end 570. The curved slot 566 may extend axially and circumferentially through a wall thickness of the first end region 562 of the endoscope end 560.

To assemble the endoscope end 560 with the cap 540, the first end 568 of the curved slot 566 may be aligned with the pin 552 of the cap 540. The endoscope end 560 may then be rotated and axially advanced to move the curved slot 566 along the pin 552. In some cases, the pin 552 may contact the second end 570 of the curved slot 566. However, this is not required. A first end surface of the endoscope end 560 may abut or contact the first end region 546 of the cap 540 before the pin 552 reaches the second end 570 of the curved slot 566. It is contemplated that the first end region 546 may have an outer diameter that is approximately the same as or greater than the first end region 562 of the endoscope end 560 to fluidly seal the gas/lens wash supply tube 240*c*, 245*c*. While not explicitly shown in FIG. 10, the sealing member 554 may contact an inner surface of the endoscope end 560 to fluidly seal the endoscope end 560. The assembly method of the endoscope end 560 with the cap 540 may vary based on the configuration of the endoscope end 560.

The endoscope end 560 may be secured to the cap 540 before positioning the clamp 520 on the post 504 or after, as desired. It is contemplated that the clamp 520 may be positioned above the water bottle (e.g., water bottle 270) such that siphoning is prevented. Coupling the endoscope end 560 to the post 504 via the cap 540 and clamp 520 may not only prevent water leaks, but also prevent the endoscope end from contacting the floor or other surfaces thus reducing the likelihood of contamination.

In some embodiments, the endoscope end 560 of the gas/lens wash supply tube 240*c*, 245*c* may be secured to the post 504 without the use of a cap 540. For example, the clamp 520 may be removed from the post 504 and the gas/lens wash supply tube 240*c*, 245*c* may be positioned within the cut-out region 534. The clamp 520 may then be secured to the post 504. It is contemplated that the cut-out region 534 may grip the gas/lens wash supply tube 240*c*, 245*c* to secure the gas/lens wash supply tube 240*c*, 245*c*. Alternatively, or additionally, the endoscope end 560 of the gas/lens wash supply tube 240*c*, 245*c* may have a cross-sectional dimension greater than the cut-out region 534. The endoscope end 560 of the gas/lens wash supply tube 240*c*, 245*c* may be positioned above the cut-out region 534 when the clamp 520 is secured to the post 504 such that if the of the gas/lens wash supply tube 240*c*, 245*c* slides down due to gravity, the endoscope end 560 prevents the endoscope end 560 of the gas/lens wash supply tube 240*c*, 245*c* from disengaging from the cut-out region 534.

In yet another example, a strap may be used to secure the gas/lens wash supply tube 240*c*, 245*c* to the post 504. For example, the strap may include a plurality of holes and a buckle, similar in form and function to a belt, that allow the gas/lens wash supply tube 240*c*, 245*c* to be releasably secured to the post 504 with the endoscope end 560 of the gas/lens wash supply tube 240*c*, 245*c* above the water bottle to prevent siphoning. In some cases, the strap may be used to secure more than one tube set to the post 504. In yet other examples, the cap 540 may be independent of the clamp 520 and may include a pin configured to directly engage the one or more pin holes 506 of the post 504.

Figure 11B:
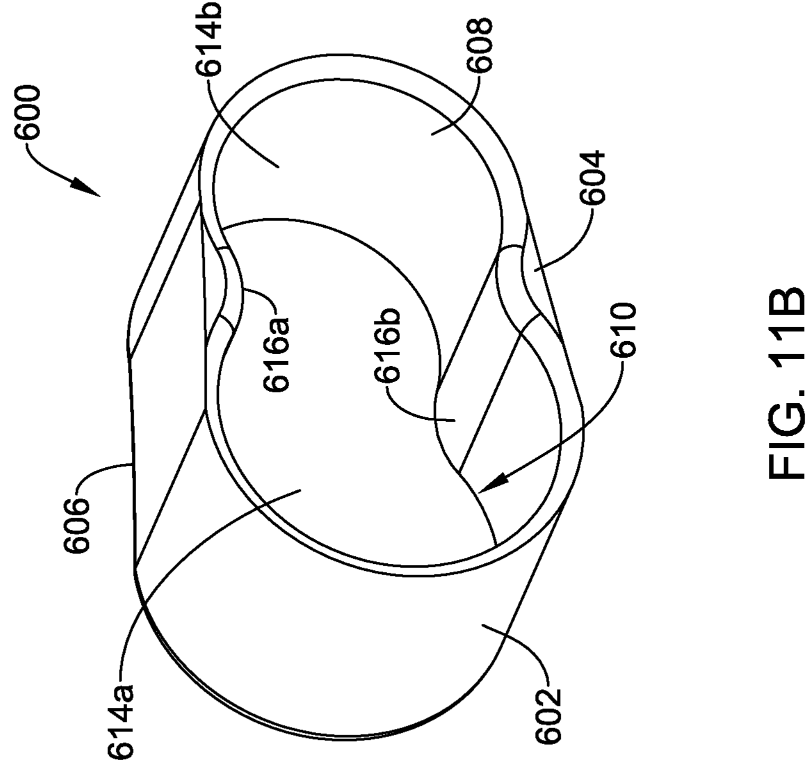
FIG. 11B depicts a rear perspective view of the illustrative cap of FIG. 11A.
Figure 11A:
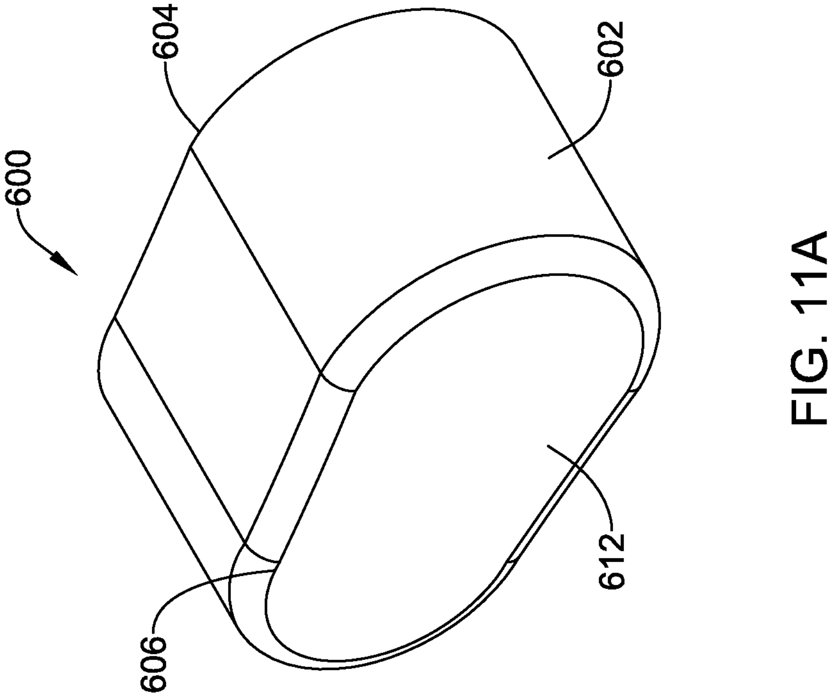
FIG. 11A depicts a front perspective view of another illustrative cap configured to be secured to an endoscope end of the water supply tubing.

FIG. 11A depicts a front perspective view of an illustrative cap 600 configured to be secured to an endoscope end of the gas/lens wash supply tubing 240*c*, 245*c* and FIG. 11B depicts a rear perspective view of the illustrative cap 600 of FIG. 11A. The cap 600 may include a body or housing 602 extending from a first end 604 to a second end 606. The first end 604 may define an opening or aperture 608 in communication with an internal cavity 610 of the housing 602. The second end 606 may include an end cap or wall 612 such that the cavity 610 does not extend through an entire length of the cap 600. The cavity 610 may include a first region 614*a* and a second region 614*b* with a pair of inwardly curved surfaces 616*a-b* disposed therebetween. It is contemplated that the cavity 610 may be sized and shaped to receive an endoscope end of a gas/lens wash supply tubing 240*c*, 245*c* in which the gas supply tubing 240*c* extends side-by-side with the lens wash supply tubing 245*c*. For example, the cavity 610 may be sized and shaped to an outer profile of the endoscope end of the gas/lens wash supply tubing 240*c*, 245*c*.

The cap 600 may be coupled with the endoscope end of the gas/lens wash supply tube 240*c*, 245*c* by placing the cap 600 over the endoscope end such that the endoscope end is disposed within the cavity 610. It is contemplated that the cap 600 may be releasably secured to the endoscope end through a snap fit, a friction fit, a threaded engagement, quick release mechanisms (e.g., a bayonet-style locking mechanism), or other releasable coupling mechanism. In some examples, the releasable coupling mechanism used to secure the cap 600 to the endoscope end may be determined by the type of coupling mechanism used to couple to the endoscope end to the endoscope (e.g., different brands of endoscopes may incorporate different connection types for coupling the gas/lens wash supply tubing 240*c*, 245*c* to the endoscope). For example, the cap 600 may be provided with internal threading, external threading, Luer-style fittings, etc.

When the endoscope end of the gas/lens wash supply tube 240*c*, 245*c* is inserted into the cavity 610 of the cap 600, the open end of the gas/lens wash supply tube 240*c*, 245*c* may contact the wall 612 of the second end 606 of the cap 600 to form a fluid tight seal between the endoscope end and the cap 600. This may prevent water from leaking from the open end of the gas/lens wash supply tube 240*c*, 245*c* when the gas/lens wash supply tube 240*c*, 245*c* is uncoupled from the endoscope regardless of a positioning of the gas/lens wash supply tube 240*c*, 245*c*. In some examples, a sealing member, such as, but not limited to a deformable insert may be within the cavity 610 against the wall 612 to help provide a fluid tight seal. Additionally, or alternatively, one or more O-rings or gaskets may be positioned within the cavity 610 to help maintain the connection between the cap 600 and the endoscope end of the gas/lens wash supply tube 240*c*, 245*c*. The cap 600 may be sized and shaped such that the cap 600 is disposed over the connection region of the endoscope end of the gas/lens wash supply tube 240*c*, 245*c*. Positioning the connection region of the endoscope end within the cavity 610 of the cap 600 may prevent the connection region from contacting surfaces when the gas/lens wash supply tube 240*c*, 245*c* is not coupled to an endoscope which may help prevent contamination of the endoscope end of the gas/lens wash supply tube 240*c*, 245*c* thus helping achieve infection prevention.

While the cap 600 has been shown and described as fitting over an outer surface of the endoscope end of the gas/lens wash supply tube 240*c*, 245*c*, in some examples, the cap 600 may be inserted into a lumen of the endoscope end of the gas/lens wash supply tube 240*c*, 245*c*. For example, the cap 600 may function as a plug that is inserted into the endoscope end of the gas/lens wash supply tube 240*c*, 245*c* as opposed to over an outer surface thereof. In some cases, the cap 600 may include a portion configured to be disposed within the endoscope end of the gas/lens wash supply tube 240*c*, 245*c* and a portion that extends over an outer surface thereof for infection prevention.

In some examples, the cap 600 may be tethered to the gas/lens wash supply tube 240*c*, 245*c* such that when the cap 600 is not in use, the cap 600 remains in close proximity to the gas/lens wash supply tube 240*c*, 245*c*. In other examples, when the cap 600 is not in use (e.g., when the endoscope end is coupled to an endoscope), the cap 600 may be manually removed from the connection region and placed in a storage case, similar in form and function to the case 400 described with respect to FIGS. 5-6.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

All apparatuses and methods discussed herein are examples of apparatuses and/or methods implemented in accordance with one or more principles of this disclosure. These examples are not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure.

In the foregoing description and the following claims, the following will be appreciated. The phrases "at least one", "one or more", and "and/or", as used herein, are open-ended expressions that are both conjunctive and disjunctive in operation. The term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another.

The foregoing discussion has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. One skilled in the art will appreciate that the disclosure may be used with many modifications of structure, arrangement, proportions, materials, components, and otherwise, used in the practice of the disclosure, which are particularly adapted to specific environments and operative requirements without departing from the principles of the present disclosure. For example, elements shown as integrally formed may be constructed of multiple parts or elements shown as multiple parts may be integrally formed, the operation of elements may be reversed or otherwise varied, the size or dimensions of the elements may be varied, and features and components of various embodiments may be selectively combined. The presently disclosed embodiments are therefore to be considered in all respects as illustrative and not restrictive, the scope of the claimed invention being indicated by the appended claims, and not limited to the foregoing description.

The following claims are hereby incorporated into this Detailed Description by this reference, with each claim standing on its own as a separate embodiment of the present disclosure. In the claims, the term "comprises/comprising" does not exclude the presence of other elements or steps. Furthermore, although individually listed, a plurality of means, elements or method steps may be implemented by, e.g., a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second", etc., do not preclude a plurality. Reference signs in the claims are provided merely as a clarifying example and shall not be construed as limiting the scope of the claims in any way.

The invention claimed is:

1. A system for preventing leaks from an endoscope end of a tube set for use with an endoscope, the system comprising:

a storage case, the storage case comprising:

a base including a plurality of wells;

an insert disposed in each well of the plurality of wells; and a lid configured to cover the base; and a cap having a housing extending from a first open end to a second closed end and defining a cavity between the first open end and the second closed end, the cap configured to be removably disposed within a well of the plurality of wells, wherein the insert is sized and shaped to conform to an inner surface of the cap.

2. The system of claim 1, wherein the insert comprises an embedded antibacterial or bacteriostatic material.

3. The system of claim 1, further comprising an antiseptic disposed within at least one well of the plurality of wells.

4. The system of claim 1, wherein the cap is configured to be disposed over an outer surface of the endoscope end of the tube set.

5. The system of claim 1, further comprising a sealing member disposed within the cavity of the cap.

6. The system of claim 1, wherein the cap further comprises a coupling mechanism, the coupling mechanism configured to releasably couple the cap to the endoscope end of the tube set.

7. A system for preventing leaks from an endoscope end of a tube set for use with an endoscope, the system comprising:

a storage case, the storage case comprising:

a base including a plurality of wells;

an insert disposed in each well of the plurality of wells; and a lid configured to cover the base; and a cap having a housing extending from a first open end to a second closed end and defining a cavity between the first open end and the second closed end, the cap configured to be removably disposed within a well of the plurality of wells, wherein the insert comprises a perforated foam.

8. The system of claim 7, wherein the insert comprises an embedded antibacterial or bacteriostatic material.

9. The system of claim 7, further comprising an antiseptic disposed within at least one well of the plurality of wells.

10. The system of claim 7, wherein the cap is configured to be disposed over an outer surface of the endoscope end of the tube set.

11. The system of claim 7, further comprising a sealing member disposed within the cavity of the cap.

12. The system of claim 7, wherein the cap further comprises a coupling mechanism, the coupling mechanism configured to releasably couple the cap to the endoscope end of the tube set.

* * * * *